United States Patent [19]

DiGiacomo et al.

[11] 4,276,409

[45] Jun. 30, 1981

[54] LAYERED CYANO END TERMINATED ORGANOPHOSPHORUS INORGANIC POLYMERS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 54,107

[22] Filed: Jul. 2, 1979

[51] Int. Cl.$^3$ .................... C08G 67/00; C08G 73/00; C08G 79/04
[52] U.S. Cl. ................... 528/362; 260/429.1; 260/429.2; 260/429.3; 260/429.5; 260/435 R; 528/395
[58] Field of Search ............................. 528/362, 395

[56] References Cited

U.S. PATENT DOCUMENTS

| | | | |
|---|---|---|---|
| 2,512,063 | 6/1950 | Kreidl et al. | 528/395 |
| 3,415,781 | 12/1968 | Block et al. | 528/395 |
| 3,663,460 | 5/1972 | Block et al. | 260/33.6 R |
| 3,681,265 | 8/1972 | Krueger | 528/271 |

OTHER PUBLICATIONS

Journal of Inorganic & Nuclear Chemistry, vol. 40, pp. 1113-1117, Jun. 1978, (Costantino et al.).

*Primary Examiner*—Wilbert J. Briggs, Sr.
*Attorney, Agent, or Firm*—Christie, Parker & Hale

[57] ABSTRACT

Cyano-organophosphorus compounds react by a metathesis reaction in a liquid medium with tetravalent metal ions yielding layered crystalline to amorphous inorganic polymers having the empirical formula $M(O_3PRCN)_2$ or $M(O_3PORCN)_2$ where M is a tetravalent metal and R is a an organic group covalently bonded to phosphorus and the terminal cyano group. One use for the compounds is as ion complexers.

14 Claims, 9 Drawing Figures

LAYERED CYANO END TERMINATED ORGANOPHOSPHORUS INORGANIC POLYMERS

BACKGROUND OF THE INVENTION

This application is related to applications Ser. No. 945,971, filed Sept. 26, 1978 and now U.S. Pat. No. 4,232,146, issued Nov. 4, 1980 titled "Process for Preparing Layered Organophosphorus Inorganic Polymers," Ser. No. 952,228, filed on Oct. 17, 1978 and now U.S. Pat. No. 4,235,990, issued Nov. 25, 1980 titled "Layered Carboxy End Terminated Organophosphorus Inorganic Polymers," Ser. No. 966,197 filed Dec. 4, 1978 and now U.S. Pat. No. 4,235,991, issued Nov. 25, 1980 titled "Layered Sulfonate End Terminated Organophosphorus Inorganic Polymers," Ser. No. 7,275, filed Jan. 29, 1979, now abandoned and titled "Layered Zirconium bis(benzenephosphonate) Inorganic Polymers", Ser. No. 43,810 filed May 30, 1979 and titled "Process for Preparing Organophosphorus Inorganic Polymers", and Ser. No. 54,097, filed concurrently with this application and titled "Layered Organophosphorus Inorganic Polymers Containing Mercapto or Thio Groups", the entire disclosures of which are incorporated herein by this reference.

The present invention is directed to solid inorganic polymers having cyano groups anchored to the surfaces of the polymers. The polymers formed can be layered crystals which display intercalation activity, or they can be partially or totally amorphous.

The interface surfaces of solids are responsive regions of chemical and physical action. Many practical chemical and physical phenomena such as absorption, corrosion, inhibition, heterogeneous catalysis, lubrication, ion exchange activity, adhesion and wetting and electrochemical activity occur on or as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in the active sites which arises from the nature of their surface structure. Furthermore much of the active sites are usually buried within the surface, and as a result of these two factors, elevated temperature and low conversions are typically required to make a process effective. Exceptions in which homogeneous agents have been used include the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the nonuniform situation of sites which has manifested itself in loss of expected selectivity, activity and even in attrition.

Figure 1:
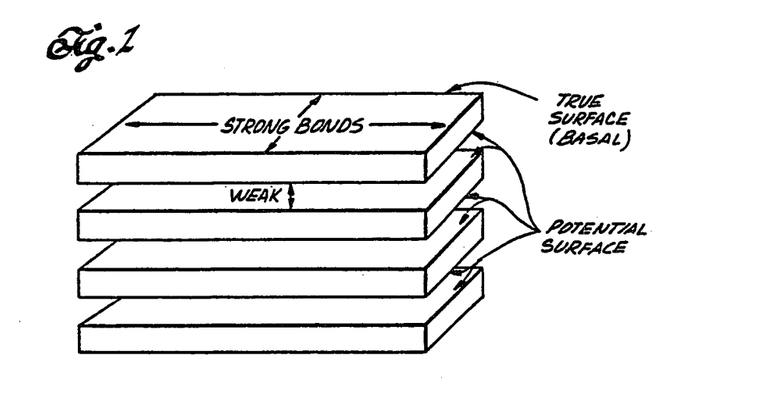
FIG. 1 illustrates a layered microcrystal. Each lamellar slab is formed of strong covalent bonds and has a thickness of about 10 atoms.

Many inorganic solids crystallize with a layered structure and present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

Figure 2:
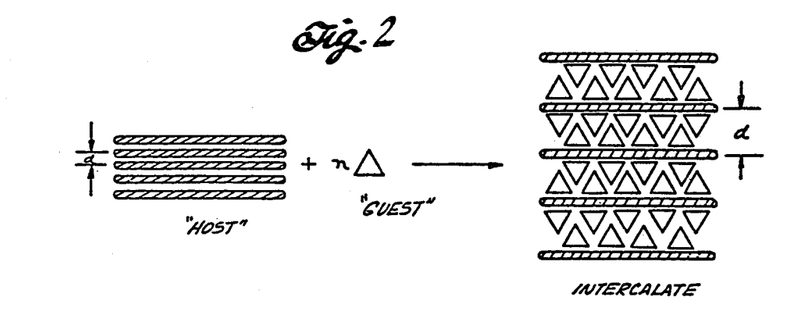
FIG. 2 illustrates intercalation where the interlayer distance is shown as "d".

In this process, designated "intercalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, the potential surface is greater than the actual surface by a factor of the number of lamella composing the crystal. This value is typically on the order of $10^2$–$10^4$. Although edge surface is practically insignificant compared to basal surface, it is critical to the rate of intercalation, since the inclusion process always occurs via the edges. This is because bonding within the sheets is strong, and therefore, penetration of the sheets is an unlikely route into the crystal.

Previous studies of the intercalative behavior of layered compounds have mainly been conducted by solid state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective fixation or catalytic conversion, specific groups must be present which effect such activity. There might also be some preferable geometric environment about each site, as well as some optimal site-to-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

Figure 3:
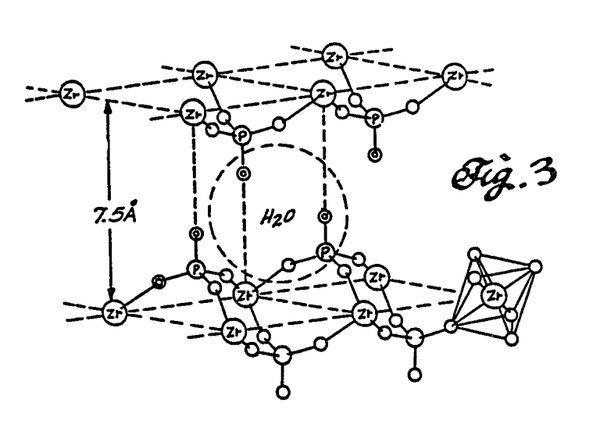
FIG. 3 illustrates the accepted structure for zirconium phosphate and spacing between layers. The dashed lines between zirconium (Zr) atoms is to establish the plane between them. In the drawing P=Phosphorus, O=Oxygen and water of hydration is shown.

One of the few layered compounds which have available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable and non-toxic.

Quite a bit of work has been conducted on the zirconium phosphate, mainly because it has been found to be a promising inorganic cation exchanger for alkali, ammonium and actinide ions, see Alberti, "Accounts of Chemical Res." 11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. A. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 28, (1976). This product is composed of a bilayer of anchored ethonolic groups aimed into interlayers. The initial layer-layer repeat distance is expanded from about 7.5 Å to 15 Å, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

A very recently reported effort in the field is Alberti, et al, "J. Inorg. Nucl. Chem.", 40, 1113 (1978) which is incorporated herein by reference. A method similar to that of this invention for the preparation of zirconium bis(benzenephosphonate), zirconium bis(hydroxymethanephosphonate) monohydrate, and zirconium bis(-monoethylphosphate) is described, with descriptions of the properties for these products.

SUMMARY OF INVENTION

According to the present invention there is provided inorganic polymers having cyano groups pendant to phosphorous atoms wherein the phosphorus atoms are, in turn, linked by oxygen to tetravalent metal atoms. The pendant cyano groups are coupled to phosphorus directly or through an organic group.

Compounds provided in accordance with the invention are inorganic polymers providing pendant cyano groups and which include units of the formula:

wherein R is an organo group in which the phosphorus is structurally linked through each of the available oxygens to a tetravalent metal selected from the group consisting of zirconium, cerium, thorium, uranium, hafnium, lead, titanium, and mixtures thereof and wherein the molar ratio of phosphorus to tetravalent metal in said inorganic polymer is about 2 to 1.

Cyano homopolymers which are inorganic phosphorus polymers have the empirical formula:

wherein R is as defined above and M is a tetravalent metal.

The compounds of the invention are formed by a liquid media reaction in which at least one cyano phosphorus-acid compound of the formula:

wherein R is as defined above, is reacted with at least one tetravalent metal ion selected from the group consisting of zirconium, cerium, thorium, uranium, lead, hafnium, titanium and mixtures thereof. The molar ratio of phosphorus to the tetravalent metal in the product is 2 to 1. Reaction, however, preferably occurs in the presence of an excess of phosphorus containing acid reactants to consume all of the metal ions and the metal ion is provided as a compound soluble in the liquid media.

Introduction of the cyano group may be carried out before or after formation of the organophosphorus inorganic polymer, resulting in different degrees of crystallinity.

Other organophosphorus acid compounds may be present for reaction to form part of the inorganic polymer which is the product of the reaction. These organophosphorus acid compounds need not contain cyano functions. They may contain substituents which have functional groups that interact with the cyano groups in the product. Donor functional groups such as sulfonate, ether, ester, amide, oxo, carboxy, hydroxy, sulfide, hydrosulfide and the like influence the ion binding activity of the cyano groups. These substituents may also contain ionic groups. The cyano group would modify the reactivity of such ionic groups. Phosphoric and/or phosphorous acid can also be present as reactive diluants.

The products formed are layered crystalline to semicrystalline to amorphous in nature. The pendant cyano groups serve as ion complexers, as intermediates for the addition or substitution of other functional groups.

Multicomponent polymers, containing other organic groups interspersed with the cyano group, can be prepared. In addition, a mixture of two or more acids can be used in the preparation.

DETAILED DESCRIPTION

According to the present invention, there is provided crystalline to amorphous inorganic polymers formed of structural units of the formula:

$$M(O_3P-R-CN)_2 \text{ or } M(O_3PO-R-CN)_2$$

wherein R is an organo group covalently bonding the CN group to phosphorus and wherein each phosphorus is linked through oxygen to M, a tetravalent metal selected from the group consisting of zirconium, cerium, thorium, uranium, lead, titanium, hafnium, and mixtures thereof and wherein the molar ratio of phosphorus to tetravalent metal in said inorganic polymer is about 2 to 1.

Homopolymers are where inorganic phosphorus polymers have the empirical formula:

$$M(O_3PRCN)_2 \text{ or } M(O_3PORCN)_2$$

wherein R is as defined as above, with R linked to phosphorus by carbon or oxygen, and M is a tetravalent metal ion selected from the group consisting of zirconium, cerium, thorium, uranium, hafnium, lead, titanium and mixtures thereof to form a solid inorganic polymer precipitate in which phosphorus is linked to the metal by oxygen and the cyano-organo group is covalently bonded to the phosphorus atoms. The cyano group is pendent from the inorganic polymer. Typically, the tetravalent metal ion is provided as a soluble salt MX where M is tetravalent metal as defined above and X is the anion(s) of the salt. Typical anions include halides such as $Cl^-$, $HSO_4^{-1}$, $SO_4^{-2}$, $O_2C-CH_3^{-1}$, $NO_3^{-1}$, $O^{-2}$ and the like.

The polymeric reaction products formed have been found to be layered crystalline or semi-crystalline in nature and, as such, provide layered structures similar to zirconium phosphate. The amorphous portion of polymers possesses a large quantity of available pendent groups and is similar to silica gel.

By the term "cyano acid compound," as used herein, there is meant a compound of the formula:

$$(HO)_2OPRCN \text{ or } (HO)_2OPORCN$$

wherein RCN is any organo group which will replace an hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is preferred with coupling through carbon particularly preferred.

By the term "organophosphorus acid compound" as used herein, there is meant compounds other than cyano terminated compounds of the formula:

$$[(HO)_2OP]_xR' \text{ or } [(HO)_2OPO]_xR'$$

wherein x is 1 or 2 and R' is an organo group other than one providing the cyano group. Coupling is preferably through carbon or an oxygen-carbon group and may be used as indicated below as co-reactants or as exchange reactants.

When coupling is through carbon, the cyano phosphorus acid compound or the organophosphorus acid compound is a cyano or organo phosphonic acid and the product is a phosphonate. When coupling is through oxygen-carbon, the cyano phosphorus acid compound or organophosphorus acid compound is a cyano or organo phosphoric monoester acid and the product a phosphate.

The general reaction for phosphonic acids alone is shown in equation (1) below and for monoesters of phosphoric acid alone by equation (2).

$$M^{+4} + 2(HO)_2PRCN \rightarrow M(O_3PRCN)_2 \quad (1)$$

$$M^{+4} + 2(HO)_2P(OR'')CN \rightarrow M(O_3P(OR''))CN_2 \quad (2)$$

wherein R'' is the remainder of the organo group "R."

The product contains phosphorus to metal in a molar ratio of about 2 to 1, and the empirical formula for the product would show all groups bound to phosphorus.

In general, the choice of R will affect compound stability, the basicity of the cyano group, the hydrophilic-hydrophobic nature of the solid, interlamellar spacing, crystal size, etc.

While nowise limiting, the R groups attachable may be saturated or unsaturated, substituted and unsubstituted and include, among others, alkyl, alkylene, alkyne, aryl, alkylaryl, heterocyclic and the like or can be partially or wholly halogen substituted, e.g., perfluoralkyl. Typically, the R group will contain from about 1 to about 17 carbon atoms, preferably from 1 to about 8 carbon atoms.

While nowise limiting, the R' groups attachable to organophosphorus acid compounds may be saturated and unsaturated, substituted and unsubstituted and include among others, alkylene, alkyloxy, alkyne, aryl, haloalky, alkylaryl, aryloxy, mercaptoalkyl, aminoalkyl, morpholinoalkyl, sulfoalkyl, phenoxyalky, beta-diketo alkyl, alkyl, cyanoalkyl, cyanoalkoxy, heterocyclic and the like or can be partially or wholly halogen substituted.

Figure 4:
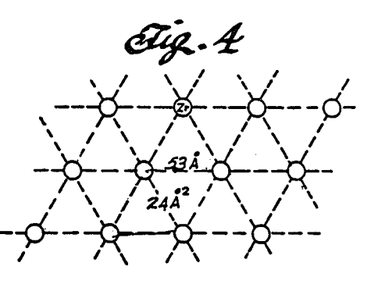
FIG. 4 illustrates a projection of zirconium plane showing accepted spacing between Zr atoms and the available linkage area.
Figure 5:
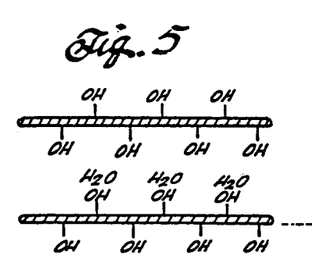
FIG. 5 is a symbolized depiction of spaced zirconium phosphate layers showing covalently bonded hydroxyl groups and water of hydration.
Figure 6:
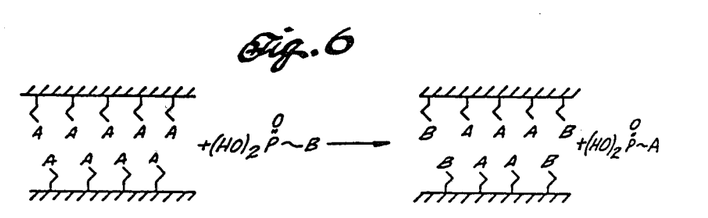
FIG. 6 illustrates an exchange reaction where anchored CN groups ("A") are to be substituted by "B", and represents the portion of the organo group linking the terminal group "A" or "B" to the crystals or the organophosphorus acid compound reactant.

In general, the organo group should occupy no more than about 25 Å² for proper spacing. This limitation is imposed by the basic crystal structure of zirconium phosphate. Referring to FIG. 4, a spacing of 5.3 Å is shown between zirconium atoms in the zirconium plane of a crystal, a total area of about 24 Å² is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than 25 Å², adjacent groups may be somewhat larger than 25 Å² and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE I

| Moiety | Minimum Area (Å²) | Moiety | Minimum Area (Å²) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50 (approx.) |
| Morpholino | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the cyano and organophosphorus acid compounds are hygroscopic, an organic solvent such as ethanol may be employed, where water interferes with the reaction or where solubility is to be promoted. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the cyano phosphorus acid compound may serve as a solvent. Typically, the liquid medium is the liquid medium in which the cyanophosphorus acid compound is formed.

For complete consumption of the tetravalent compound, the amount of acid employed should be sufficient to provide two moles of phosphorus per mole of tetravalent metal. An excess is preferred. Phosphorus acid and/or phosphoric acid, if present, will enter into the reaction and provide an inorganic polymer diluted in respect to the cyano groups in proportion to the amount of phosphorus or phosphoric acid employed.

Reaction is virtually instantaneous at all temperatures leading to precipitation of layered crystalline and semi-crystalline inorganic polymer solids.

An amorphous phase may appear as a gel similar to silica gel. The gel can be crystallized by extended reflux in the reaction medium, usually from about 5 to 15 hours. The semi-crystalline product is characterized by a rather broad X-ray powder pattern.

The presence of sequestering agents for the metal ion slows down the reaction and also leads to more highly crystalline products. For instance, hydrogen fluoride is a sequestering agent for zirconium and nitrate ion a sequestering agent for thorium. Both slow the reaction and promote the formation of highly crystalline end products.

As compared to zirconium phosphate forming crystals of 1–5 microns, crystals of 100 to 1000 microns in size have been prepared.

The process of preparation permits a wide variety of inorganic polymers to be formed having the characteristics of the organo group protected by the inorganic polymer structure and with subsequent exchange or substitution reactions, the formation of other inorganic polymers. Polymers formed may be block, random and the like.

For instance, a mixture of cyano phosphorus acid compounds, mixtures of cyano and organophosphorus acids and organo phosphorus acid compounds may be reacted with one or more of the tetravalent metal ions. If phosphorous and/or phosphoric acid is present, it will enter into the reaction as a reaction diluent.

The high surface area of the crystalline products also make them useful for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from laboratory chemical suppliers. The products formed are insoluble in normal solvents and do not sublime. However, the combined weight of yield data, elemental analysis, spectroscopy and powder diffraction results confirm the compositions reported with good reliability.

X-ray powder patterns were run on a Phillips diffractometer using CuK radiation.

Thermal analysis was conducted on a Mettler instrument. Infrared spectra were obtained with a Beckman spectrophotometer.

EXAMPLE 1

A 6.277 g portion of barium 2-cyanoethylphosphate was placed into an Erlenmeyer flask and slurried in deionized water. About 2 ml. of concentrated hydrochloric acid was added to form the compound 2-cyanoethylphosphoric acid. The flask was fitted with a Tuttle cover (Fisher Scientific Company Cat. No. 10-042) and the contents heated to boiling. To this was added 1.100 g of $ZrOCl_2.8H_2O$. A white precipitate formed immediately, and the mixture was heated and refluxed for about one day. The solution was inadvertently evaporated to dryness during this time.

The solid material was slurried with dilute acid and filtered, then the solid was washed successively with deionized water, acetone and ethyl ether. After drying at 60° C. for about three hours, the solid product weighed 1.393 g.

Figure 7:
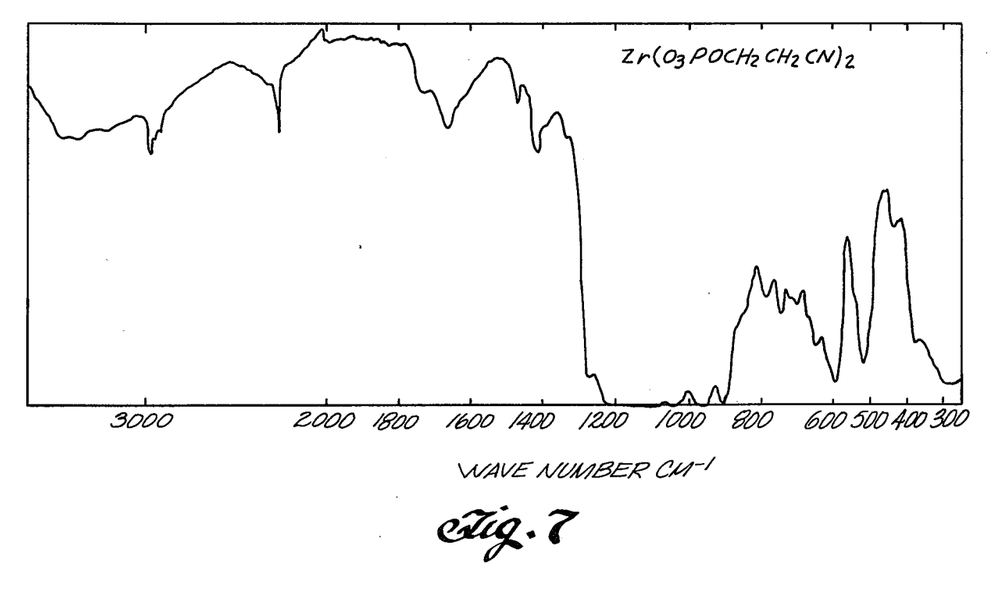
FIG. 7 is an infrared absorption spectrum for the compound zirconium bis(2-cyanoethylphosphate), as prepared in Example 1.

Elemental analysis of the solid yielded the following composition: 17.60%C, 2.76%H and 6.22%N. The infrared absorption data, shown as FIG. 7, indicates the presence of a cyano group and show the alkane stretch, as well as the presence of water. A structural formula of $Zr(O_3POCH_2CH_2CN)_2.H_2O$, zirconium bis(2-cyanoethylphosphate), can be inferred from the analytical data and the reaction yield, which is 100.2% of the theoretical yield calculated for that formula.

Figure 8:
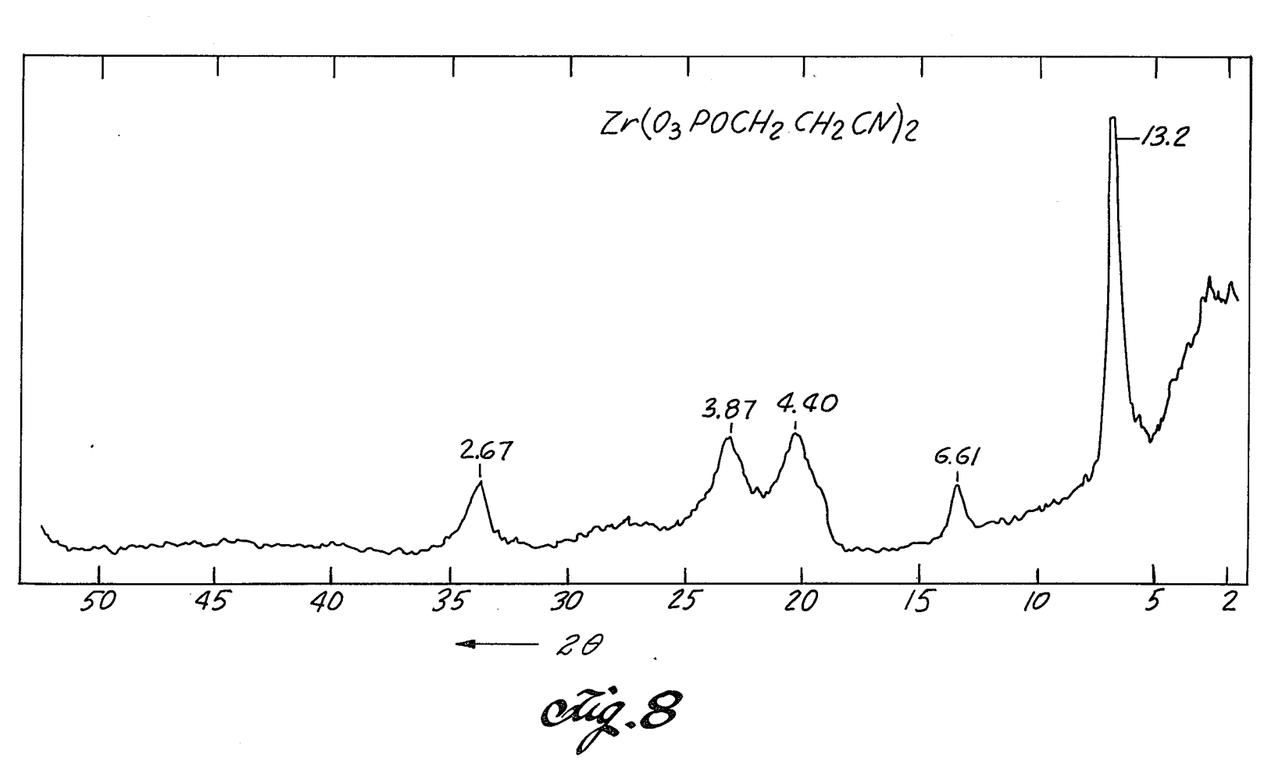
FIG. 8 is an X-ray powder defraction pattern for the compound zirconium bis(2-cyanoethylphosphate), as prepared in Example 1.

An X-ray powder diffraction pattern of the product, shown as FIG. 8, indicates the highly crystalline nature of the compound, and shows an interlayer spacing of 13.2 Å.

Thermogravimetric analysis of the solid shows a decomposition beginning at about 175° C., achieving its maximum rate at about 300° C., and being complete by about 375° C.

EXAMPLE 2

The compound of Example 1 was prepared by slurrying 6.311 g of barium 2-cyanoethylphosphate in deionized water, acidifying with 2 ml of concentrated hydrochloric acid and mixing with 2.199 g of zirconyl chloride octahydrate.

A white precipitate formed, and the mixture (of about 100 ml total volume) was heated and maintained at about 90° C. over a weekend.

The solid was isolated by filtration and washed successively with deionized water, acetone and ethyl ether, then dried at about 50° C. for about one hour. The yield was 2.886 g.

Elemental analysis of the solid yielded the following: 17.12%C and 2.89%H. Infrared absorption data were very similar to those obtained in Example 1. The X-ray powder diffraction pattern for this solid indicates a semicrystalline state, with very low reflection intensities.

EXAMPLE 3

A 4.652 g portion of diethyl cyanomethylphosphonate, 10 ml of deionized water and 20.0 g of 47% by weight hydrobromic acid were placed into a 250 ml round bottom heated and stirred flask. The flask was fitted with a Barrett water trap having a water cooled Friedrich condenser on its top.

The mixture was heated, and the reaction (which forms ethyl bromide and cyanomethylphosphonic acid) monitored by observing the volume of ethyl bromide which collected in the trap, a 3.95 ml volume of ethyl bromide being the theoretical yield. The reaction was about 30% complete after 10 minutes, and then slowed. After about 30 minutes, 2.9 ml had been collected (about 75% yield), after which the reaction appeared to cease. Water was collected above the ethyl bromide in the trap.

To the mixture remaining in the flask was added 4.36 g of zirconyl chloride octahydrate and deionized water to make about 50 ml total volume. A white precipitate formed and the mixture was heated to boiling, then refluxed overnight.

After filtering, the solid product was washed successively with deionized water, acetone and ethyl ether, then dried at about 55° C. for a few hours. The solid weighed 4.549 g, representing 99.6% of the theoretical yield for $Zr(O_3PCH_2CN)_2.H_2O$, zirconium bis(cyanomethylphosphonate).

Figure 9:
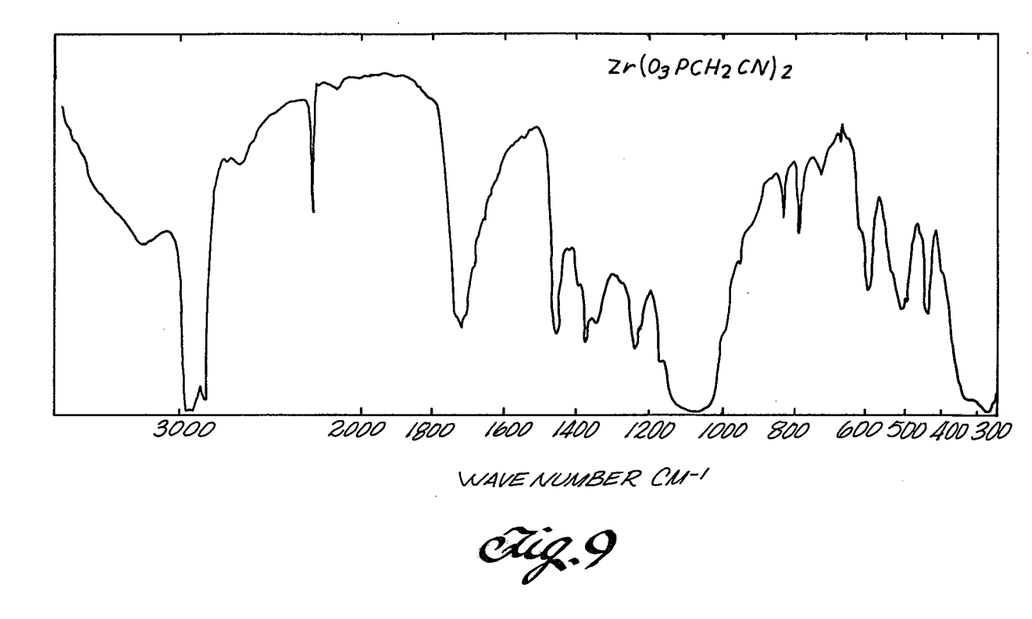
FIG. 9 is an infrared absorption spectrum for the compound zirconium bis(cyanomethylphosphonate), as prepared in Example 3.

Elemental analysis of the solid gave the following composition: 14.60%C, 2.13%H and 3.94%N. The infrared absorption data, shown as FIG. 9, indicate the presence of a cyano group and water.

An X-ray powder diffraction pattern of the product, shown as FIG. 10, indicates the highly crystalline nature of the compound, and shows an interlayer spacing of 10.8 A.

EXAMPLE 4

In an attempt to prepare the compound of Example 3 without hydrolyzing the cyano group, 4.045 g of diethyl cyanomethylphosphonate and 2.034 g of zirconyl chloride octahydrate in about 15 ml of deionized water were placed into a flask, heated and permitted to reflux. No precipitation was observed for the first two hours; only a clear yellow solution was present.

Two drops of concentrated hydrochloric acid were added and, after about five minutes, a white precipitate quickly formed. A 40 ml portion of deionized water was added to fluidize the slurry, and refluxing allowed to continue overnight.

After filtering, the solid product was washed successively with deionized water, ethanol and ethyl ether, then dried at about 100° C. for about one hour. The yield was 3.839 g, which is 102% of the expected weight of zirconium bis(cyanomethylphosphonate) if there is no water of hydration present.

Elemental analysis of the solid yielded the following composition: 16.53%C, 2.76%H and 5.54%N. The infrared absorption data show the presence of a cyano group. An X-ray powder diffraction pattern shows the solid to be essentially amorphous.

EXAMPLE 5

To a 250 ml three-necked flask fitted with a reflux condenser, stirrer and addition funnel was charged 5.8 g of barium 2-cyanoethylphosphate, 100 ml of deionized water and 2 ml of concentrated hydrochloric acid. The slurry was stirred until all salts had dissolved, and 3.8 g of uranium tetrachloride dissolved in 50 ml of deionized water was added, dropwise. A green solid began to form almost immediately. After the addition was complete, the mixture was heated to about 80° C. and maintained at that temperature for about one hour.

The solid was isolated by filtration, washed successively with deionized water, acetone and ethyl ether, then dried at about 50° C., yielding 5.02 g of product. This represents 94% of the theoretical yield for $U(O_3POCH_2CH_2CN)_2$, uranium bis(2-cyanoethylphosphate).

The infrared absorption spectrum indicates the presence of a cyano group. Elemental analysis of the solid yielded the following composition: 11.67%C and 2.12%H. The solid was semi-crystalline to crystalline, and X-ray powder diffraction indicated an interlayer spacing of 13.8 Å.

EXAMPLE 6

An experiment was performed to determine the ability of a layered cyano end terminated polymer to extract copper ions from aqueous solution. A 0.09 g portion of the zirconium bis(2-cyanoethylphosphate) compound which was prepared in Example 1 was mixed with 5 ml of a solution containing 0.1 M $CuSO_4$, 0.5 M CH₃COONa and 0.5 M CH₃COOH. The mixture was permitted to stand for a day and a portion of the supernatant liquid was decanted and analyzed for copper.

The initial copper solution contained 6.45 g/l Cu and the "extracted" solution contained 5.94 g/l Cu, indicating an extraction of 0.51 g/l copper.

EXAMPLE 7

The experiment of Example 6 was repeated using 0.091 g of the compound and 5 ml of unbuffered 0.1 M CuSO₄ solution.

Analyses of the initial copper solution gave a value of 6.33 g/l Cu, and the "extracted" solution contained 5.89 g/l Cu, indicating an extraction of 0.44 g/l copper.

EXAMPLE 8

An experiment to determine the ability of zirconium bis(2-cyanoethylphosphate) to extract silver ions from aqueous solution was performed. A 0.090 g portion of the compound prepared in Example 1 was mixed with 5 ml of 0.1 M AgNO₃ solution, allowed to stand for several days and a portion of the liquid decanted for analysis.

The initial silver solution contained 10.8 g/l Ag and the "extracted" solution contained 9.82 g/l Ag, showing an extraction of 0.98 g/l Ag.

EXAMPLE 9

Another method of preparation which minimizes hydrolysis of the cyano group involves conversion of dialkyl phosphonate esters to bis(trimethylsilyl) esters, followed by hydrolysis to the phosphonic acid using an equivalent amount of water, and then reacting with tetravalent metal ion.

In an experiment to demonstrate this method, 4.0 g of diethyl-3-cyanopropyl phosphonate in 12 ml of carbon tetrachloride, was treated with 5.6 ml of trimethylsilyl iodide. This was cooled to 0° C. and stirred for 10 minutes, and allowed to warm to room temperature, forming bis(trimethylsilyl)-3-cyanopropyl phosphonate.

A 10 ml portion of the reaction mixture was treated with 2.5 ml of deionized water, forming two phases. The upper (aqueous) phase contained 3-cyanopropyl phosphonic acid, and was separated. The aqueous phase was diluted with about 20 ml of deionized water, and 4.8 g of zirconyl chloride octahydrate in 10 ml of water was added, forming a white precipitate.

The solid product, zirconium bis(3-cyanopropyl)-phosphonate, was isolated by filtration, was successively washed with water, acetone and ethyl ether, then dried at about 35° C. The yield was 1.8 g. The infrared absorption spectrum shows the presence of a cyano group by a sharp absorption at 2240 cm⁻¹.

EXAMPLE 10

By the method of Example 9, diethyl 2-cyanoethyl phosphonate is converted to zirconium bis(2-cyanoethyl)phosphonate, that is, reaction with trimethylsilyl iodide, hydrolysis with water, and reaction with zirconyl chloride.

What is claimed is:

1. Inorganic phosphorus containing polymers providing pendant cyano groups, and which include units of the formula $$M(O_3PRCN)_2$$

wherein R is an organo group and the oxygen atoms are bonded to phosphorus and structurally linked to M, which is one or more tetravalent metals selected from the group consisting of zirconium, cerium, thorium, uranium, hafnium, lead and titanium, and wherein the molar ratio of phosphorus to tetravalent metal in the inorganic phosphorus containing polymer is about 2 to 1.

2. Inorganic phosphorus containing polymers as in claim 1 in which R contains from about 1 to about 17 carbon atoms.

3. Inorganic phosphorus containing polymers as in claim 1 in which R contains from about 1 to about 8 carbon atoms.

4. Inorganic phosphonate polymers having the empirical formula $$M(O_3PRCN)_2$$

wherein R is an organo group which is bonded to phosphorus through carbon and M is one or more tetravalent metal ions selected from the group consisting of zirconium, cerium, thorium, uranium, hafnium, lead and titanium.

5. Inorganic phosphonate polymers as in claim 4 in which R contains from about 1 to about 17 carbon atoms.

6. Inorganic phosphonate polymers as in claim 4 in which R contains from about 1 to about 8 carbon atoms.

7. Inorganic phosphate polymers having the empirical formula $$M(O_3PORCN)_2$$

wherein R is an organo group which is bonded to phosphorus through oxygen and M is one or more tetravalent metal ions selected from the group consisting of zirconium, cerium, thorium, uranium, hafnium, lead and titanium.

8. Inorganic phosphate polymers as in claim 7 in which R contains from about 1 to about 17 carbon atoms.

9. Inorganic phosphate polymers as in claim 7 in which R contains from about 1 to about 8 carbon atoms.

10. Inorganic phosphonate polymers of zirconium bis(cyanomethylphosphonate).

11. Inorganic phosphate polymers of zirconium bis(2-cyanoethylphosphate).

12. Inorganic phosphate polymers of uranium bis(2-cyanoethylphosphate).

13. Inorganic phosphonate polymers of zirconium bis(3-cyanopropyl)phosphonate.

14. Inorganic phosphonate polymers of zirconium bis(2-cyanoethyl)phosphonate.

* * * * *